(12) United States Patent
Rantala et al.

(10) Patent No.: US 6,912,413 B2
(45) Date of Patent: Jun. 28, 2005

(54) PULSE OXIMETER

(75) Inventors: Börje Rantala, Helsinki (FI); Aki Backman, Helsinki (FI)

(73) Assignee: GE Healthcare Finland OY (FI)

( * ) Notice: Subject to any disclaimer, the term of this patent is extended or adjusted under 35 U.S.C. 154(b) by 0 days.

(21) Appl. No.: 10/661,012

(22) Filed: Sep. 12, 2003

(65) Prior Publication Data

US 2004/0054269 A1 Mar. 18, 2004

Related U.S. Application Data

(60) Provisional application No. 60/410,526, filed on Sep. 13, 2002.

(51) Int. Cl.[7] ................................................ A61B 5/00
(52) U.S. Cl. ..................................... 600/322; 600/330
(58) Field of Search ............................... 600/322–324, 600/330

(56) References Cited

U.S. PATENT DOCUMENTS

| | | | | |
|---|---|---|---|---|
| 4,859,057 A | * | 8/1989 | Taylor et al. | 600/323 |
| 5,348,004 A | * | 9/1994 | Hollub | 600/323 |
| 6,356,774 B1 | * | 3/2002 | Bernstein et al. | 600/323 |
| 6,697,658 B2 | | 2/2004 | Al-Ali | 600/323 |
| 6,714,803 B1 | * | 3/2004 | Mortz | 600/323 |
| 6,731,967 B1 | * | 5/2004 | Turcott | 600/473 |
| 2004/0002637 A1 | * | 1/2004 | Huang et al. | 600/300 |

* cited by examiner

*Primary Examiner*—Eric F. Winakur
*Assistant Examiner*—Matthew Kremer
(74) *Attorney, Agent, or Firm*—Marsh Fischmann & Breyfogle LLP

(57) ABSTRACT

The invention relates to pulsed oximeters used to measure blood oxygenation. The current trend towards mobile oximeters has brought the problem of how to minimize power consumption without compromising on the performance of the device. To tackle this problem, the present invention provides a method for controlling optical power in a pulse oximeter. The signal-to-noise ratio of the received baseband signal is monitored, and the duty cycle of the driving pulses is controlled in dependence on the monitored signal-to-noise ratio, preferably so that the optical power is minimized within the confines of a predetermined lower threshold set for the signal-to-noise ratio. In this way the optical power is made dependent on the perfusion level of the subject, whereby the power can be controlled to a level which does not exceed that needed for the subject.

32 Claims, 3 Drawing Sheets

PULSE OXIMETER

RELATED APPLICATION

This application claims priority under 35 U.S.C. § 119 to prior U.S. Provisional Patent Application No. 60/410,526, filed Sep. 13, 2002, entitled "PULSE OXIMETER", the entire contents of which are incorporated herein as if set forth herein in full.

FIELD OF THE INVENTION

The invention relates generally to devices used for non-invasively determining the amount of at least one light absorbing substance in a subject. These devices are typically pulse oximeters used to measure the blood oxygenation of a patient. More specifically, the invention relates to the optimization of power consumption in such a device.

BACKGROUND OF THE INVENTION

Pulse oximetry is at present the standard of care for the continuous monitoring of arterial oxygen saturation ($SpO_2$). Pulse oximeters provide instantaneous in-vivo measurements of arterial oxygenation, and thereby provide early warning of arterial hypoxemia, for example.

A pulse oximeter comprises a computerized measuring unit and a probe attached to the patient, typically to his or her finger or ear lobe. The probe includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by venous blood, tissue, bone, and pigments, whereas during the systolic phase, there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

Light transmission through an ideal absorbing sample is determined by the known Lambert-Beer equation as follows:

$$I_{out} = I_{in} \epsilon^{-\epsilon DC}, \quad (1)$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known and $I_{out}$ is measured, the concentration C can be calculated.

In pulse oximetry, in order to distinguish between the two species of hemoglobin, oxyhemoglobin ($HbO_2$), and deoxy-hemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

The accuracy of a pulse oximeter is affected by several factors. This is discussed briefly in the following.

Firstly, the dyshemoglobins which do not participate in oxygen transport, i.e. methemoglobin (MetHb) and carboxy-hemogiobin (CoHb), absorb light at the wavelengths used in the measurement. Pulse oximeters are set up to measure oxygen saturation on the assumption that the patient's blood composition is the same as that of a healthy, non-smoking individual. Therefore, if these species of hemoglobin are present in higher concentrations than normal, a pulse oximeter may display erroneous data.

Secondly, intravenous dyes used for diagnostic purposes may cause considerable deviation in pulse oximeter readings. However, the effect of these dyes is short-lived since the liver purifies blood efficiently.

Thirdly, coatings such as nail polish may in practice impair the accuracy of a pulse oximeter, even though the absorption caused by them is constant, not pulsatile, and thus in theory it should not have any effect on the accuracy.

Fourthly, the optical signal may be degraded by both noise and motion artifacts. One source of noise is the ambient light received by the photodetector. Many solutions have been devised with the aim of minimizing or eliminating the effect of the movement of the patient on the signal, and the ability of a pulse oximeter to function correctly in the presence of patient motion depends on the design of the pulse oximeter. One way of canceling out the motion artifact is to use an extra wavelength for this purpose.

One of the current trends in pulse oximetry is the aim towards lower power consumption, which is essential for battery-operated oximeters, for example. These oximeters are typically mobile and must therefore be used in various locations where both the characteristics of the patient and the surrounding measurement environment may vary. A problem related to these various measurement conditions is the optimization of power consumption without compromising the performance of the device, i.e. how to guarantee reliable measurement results even in difficult measurement conditions and still keep the battery life as long as possible.

The current straightforward solution for obtaining reliable measurement results under tough measurement conditions is to increase the driving power of the LEDs. This approach is based on the transmittance of the tissue: if the level of the signal transmitted through the tissue is not enough to guarantee reliable results, the level of the transmitted signal (i.e. the amplitude of the pulse train) is increased until the level of the signal received is sufficient. This is naturally contrary to the need to save power.

It is an objective of the invention to bring about a solution by means of which it is possible to dynamically optimize the power consumption in a pulse oximeter, especially in a portable battery-operated pulse oximeter, and to maintain good performance even in tough measurement conditions, where the transmittance and/or the perfusion level, as indicated by the normalized pulsatile component, are low.

SUMMARY OF THE INVENTION

These and other objectives of the invention are accomplished in accordance with the principles of the present invention by providing a power-saving scheme which allows the pulse oximeter to use no more power than that which is needed to drive the emitters while maintaining good performance of the oximeter. In this scheme, the signal-to-noise requirements are compromised in favor of power consumption, as long as this does not compromise measurement reliability.

According to the invention, the patient-specific effect of the tissue on the measurement result is taken into account, whereby the optical power, i.e. the power supplied to activate the emitters, can be controlled to a level which is no more than what is needed for each measurement. The idea behind the invention is that the measurement results of the pulse oximeter depend on the perfusion level and on the transmittance of the tissue under illumination. Therefore, the optical power in the pulse oximeter of the invention can be controlled at each measurement occasion to a level which is the minimum sufficient for the patient in question, by monitoring the demodulated baseband signal indicative of the perfusion level of the patient and controlling the duty cycle of the driving pulses so that the optical power is minimized given a predetermined lower threshold set for the signal-to-noise ratio.

The invention provides other ways to reach the level which is enough at each time, said ways being applicable alone or in combination. These ways can also be combined with the normal increase of the amplitude of the driving pulses.

Under favorable conditions the requirements for the signal-to-noise ratio of the pulse oximeter are eased in favor of power consumption, and the optical power is dropped to the minimum level sufficient for measurement. Power is then increased only when the minimum signal-to-noise ratio ensuring a reliable measurement is not otherwise reached.

Thus, one aspect of the invention is providing a method for controlling optical power in a monitoring device intended for determining the amount of at least one light absorbing substance in a subject, the monitoring device comprising emitters for emitting radiation at a minimum of two wavelengths, driving means for activating said emitters, and a detector for receiving said radiation at said wavelengths and for producing an electrical signal in response to the radiation, the method comprising the steps of supplying driving pulses from said driving means to the emitters, the pulses having predetermined characteristics determining the optical power of the device, demodulating the electrical signal originating from said detector, whereby a baseband signal is obtained, monitoring a signal-to-noise ratio of the baseband signal, and controlling the duty cycle of the driving pulses in dependence on the monitored signal-to-noise ratio.

The duty cycle is preferably controlled so that the optical power is minimized within the confines of a predetermined lower threshold set for the signal-to-noise ratio.

Another aspect of the invention is that of providing an apparatus for non-invasively determining the amount of at least one light absorbing substance in a subject, the apparatus comprising emitters for emitting radiation at a minimum of two different wavelengths, driving means for activating said emitters, adapted to supply driving pulses to the emitters, the pulses having predetermined characteristics determining current optical power of the device, a detector for receiving said radiation at said wavelengths and producing an electrical signal in response to the radiation, a demodulator unit for demodulating the electrical signal originating from said detector, whereby a baseband signal is obtained from the demodulator unit, monitoring means for monitoring a signal-to-noise ratio of the baseband signal, and power control means, responsive to the monitoring means, for controlling the duty cycle of the driving pulses.

The power control means are preferably adapted to perform the controlling of the duty cycle so that the optical power is minimized within the confines of a predetermined lower threshold set for the signal-to-noise ratio.

The power control scheme of the present invention provides good performance even when the tissue is thick (requiring high drive current) and the perfusion (pulsatility) is low. In this case the front stage of the pulse oximeter tends to saturate, whereby a conventional pulse oximeter can no longer operate in a reliable way. In contrast, the pulse oximeter of the invention may still obtain reliable readings by widening the pulses or increasing the pulse repetition rate, thereby increasing the signal-to-noise ratio.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 4d in the appended drawings, wherein.

DETAILED DESCRIPTION OF THE INVENTION

Figure 1:
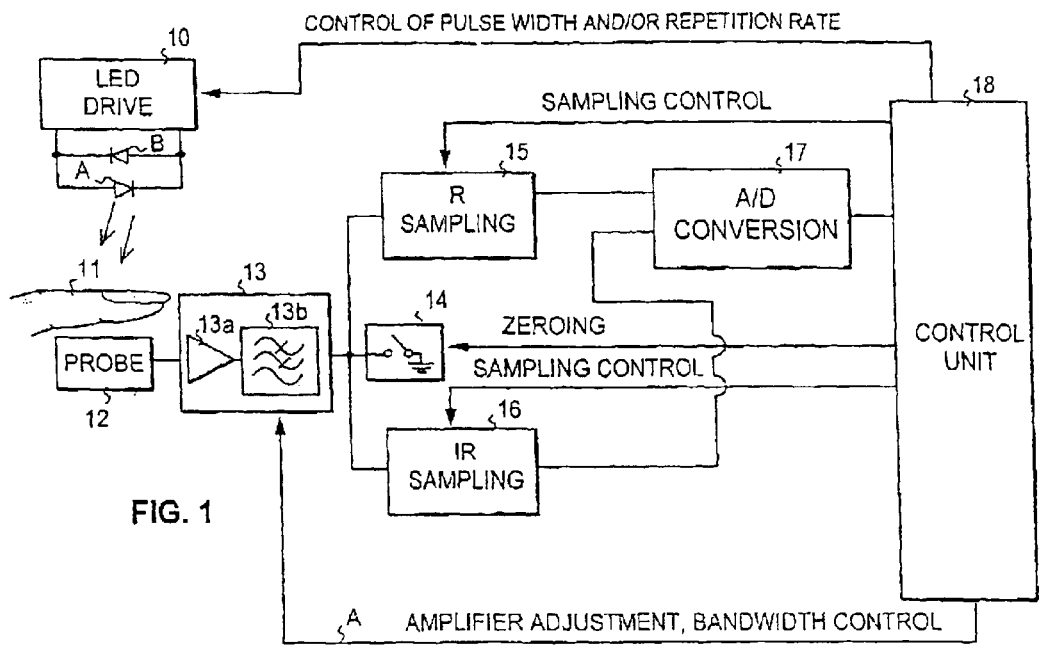
FIG. 1 illustrates a typical embodiment of a pulse oximeter according to the present invention.

FIG. 1 is a block diagram of one embodiment of a pulse oximeter according to the present invention. This embodiment is based on a traditional pulse oximeter where synchronous detection is used. At least two different LEDs, A and B, are driven by a LED drive 10. Each LED operates at a respective wavelength, and the light emitted by the LEDs passes into patient tissue, such as a finger 11. The light propagated through or reflected from the tissue is received by a probe 12 including a photodetector. The photodetector converts the optical signal received into an electrical signal and supplies it to an amplifier stage 13, which includes a controllable preamplifier 13a and a variable low-pass filter 13b. After the amplifier stage, an analog switch 14, controlled by the control unit 18, ensures that the signal is zeroed between consecutive pulses, thereby removing background light. The reception branch is then divided into two branches: the IR branch for the infrared signal and the R branch for the red signal. Each branch is preceded by an analog switch (not shown in the figure), which is controlled by the control unit 18 so that the pulses are connected to their respective branch (the R pulses to the R branch and the IR pulses to the IR branch). In each branch a sampling unit (15, 16) then takes samples of the pulses received by the branch. The control unit controls the R sampling unit so that it samples the R pulses and the IR sampling unit so that it samples the IR pulses. The sampling units typically include a sampling switch and a capacitor charged to the pulse voltage prevailing at the sampling moment. The sampled signals are then supplied to an A/D converter 17, which converts them into digitized format for the control unit 18. The synchronous detection performed in the sampling units 15 and 16 is also termed "demodulation" in this context, since it is the operation which extracts the original modulating signal from the detector signal.

In order to introduce the power-controlling scheme of the invention into a pulse oximeter of the type shown in FIG. 1, the pulse oximeter structure is modified so that the control unit 18 monitors the baseband signal-to-noise ratio (i.e. the signal-to-noise ratio of the demodulated baseband signal) and selects the optical power in dependence on the monitored ratio. The power consumption is minimized dynamically, so that when the monitored signal-to-noise ratio is low, the control unit starts to compromise on power consumption in favor of performance, thereby ensuring reliable measurement results. As discussed below, minimizing power consumption involves changing at least one parameter of the duty cycle of the pulse train driving the LEDs so that the optical power changes in the desired direction. The parameters include the pulse width and the pulse repetition rate. When the control unit decreases the pulse width, it simultaneously widens the bandwidth of the low-pass filter 13b to allow the pulse to reach essentially its full height. When the control unit increases the pulse width, it simultaneously narrows the bandwidth of the low-pass filter to decrease the amount of input noise. In addition to the pulse width and/or the repetition rate, the pulse amplitude can also be controlled.

Figure 2:
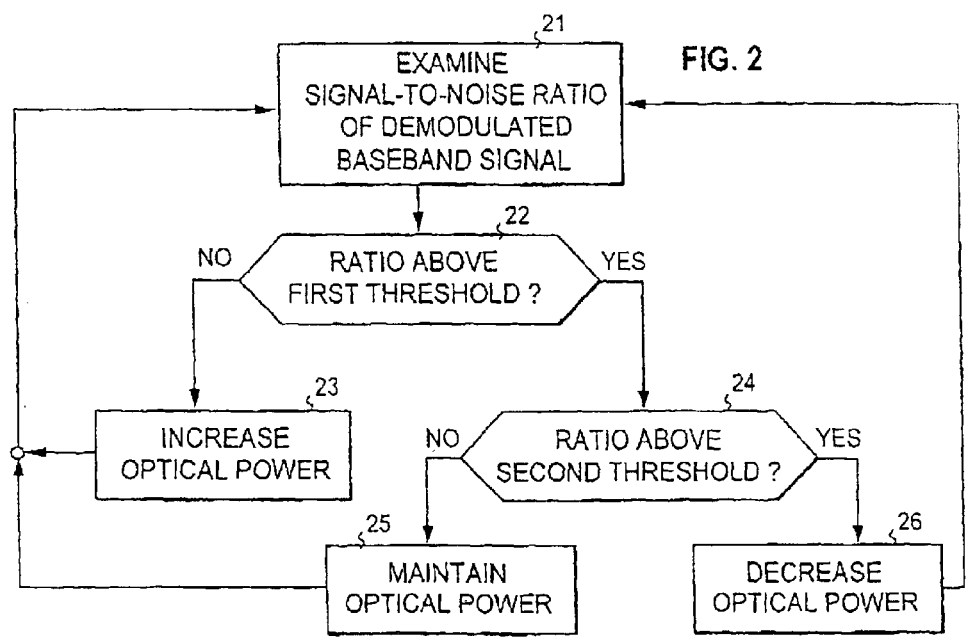
FIG. 2 is a flow diagram illustrating one embodiment of the power control scheme of the present invention.

FIG. 2 illustrates one embodiment of the power control scheme. It is assumed here that the power control scheme is implemented in the pulse oximeter of FIG. 1. As discussed above, the control unit first defines the signal-to-noise ratio of the demodulated baseband signal (step 21) and compares the ratio to a first threshold, which defines the lower limit of an acceptable signal-to-noise ratio (step 22). If the current ratio is below the first ratio, the control unit increases the optical power by changing the duty cycle of the pulse train (step 23), and the process returns to step 21 to define the signal-to-noise ratio associated with the new characteristics.

If it is detected at step 22 that the signal-to-noise ratio is above the first threshold, it is examined at step 24 whether the signal-to-noise ratio is also above the second threshold, which is slightly higher than the first threshold. If this is not the case, but the ratio is between the first and second thresholds, the current characteristics of the pulse train are maintained, i.e. the optical power is maintained at its current value (step 25). If it is detected at step 24 that the signal-to-noise ratio is above a second threshold, the duty cycle of the pulse train is changed at step 26 so that the optical power is decreased. The process then returns to step 21 to define the signal-to-noise ratio associated with the new duty cycle of the pulse train.

The optical power can be increased in several ways at step 23. The first method is to increase the pulse width, while simultaneously decreasing the bandwidth of the low-pass filter 13b, which thereby decreases the amount of input noise. The second method is to increase the pulse repetition rate in order to decrease noise aliasing, i.e. to decrease the number of harmonics being down-converted by the synchronous demodulation. In addition to these operations, the current or voltage of the pulses driving the LEDs can be increased.

Accordingly, the optical power can be decreased in several ways at step 26, whenever it is detected that the signal-to-noise requirements can easily be met. The first method is to narrow the pulses, simultaneously increasing the bandwidth of the low-pass filter 13b, thereby allowing the pulses to reach approximately their full height. The second method is to use a lower pulse repetition rate, which allows more aliasing of interference/noise in the demodulation phase due to a lower sampling rate and thus degrades the signal-to-noise ratio on the baseband. The above operations can be used alone or in combination to decrease the optical power. In addition to these operations, the current or voltage of the pulses driving the LEDs can be decreased. It is to be understood that steps 23 and 26 include the control of the bandwidth associated with the control of the pulse width.

FIG. 3a to 3d illustrate noise aliasing in a conventional high duty cycle oximeter which uses LED pulses having a duty cycle greater than 10%. The power control scheme of the present invention uses a high duty cycle pulse train only when the desired signal-to-noise ratio cannot otherwise be reached, i.e. the situation of FIG. 3a to 3d is entered at step 23 in FIG. 2. FIG. 4a to 4d correspond to FIG. 3a to 3d, respectively, except that in FIG. 4a to 4d the pulse oximeter is a narrow pulse oximeter where the LEDs are activated as briefly as possible in order to save power. This power saving mode is entered whenever conditions permit easing the signal-to-noise requirements in favor of power consumption. As to the example of FIG. 2, the power saving mode is entered in step 26, and the mode is maintained in step 25.

Figure 3A:
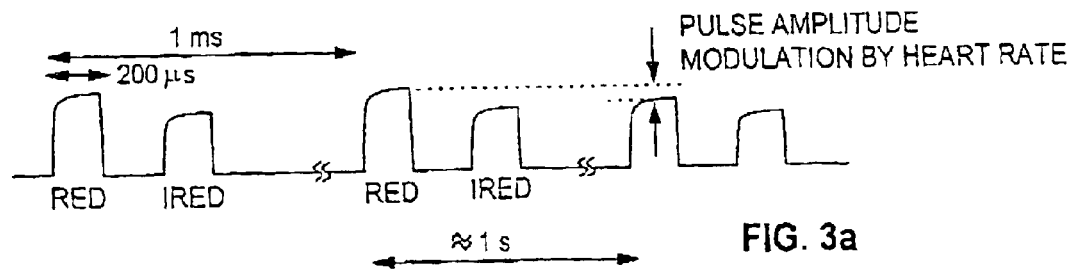
FIG. 3a illustrates the timing sequence of the detector signal when a high duty cycle pulse sequence is used.
Figure 3B:
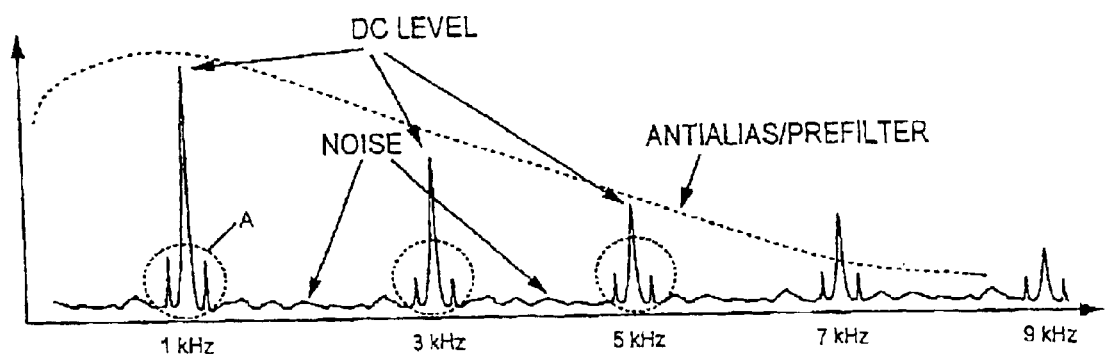
FIGS. 3b and 3c illustrate the frequency spectrum of a detector signal according to FIG. 3a, FIG. 3d illustrates the spectrum of the baseband signal obtained from the signal of FIG. 3b after demodulation.
Figure 3C:
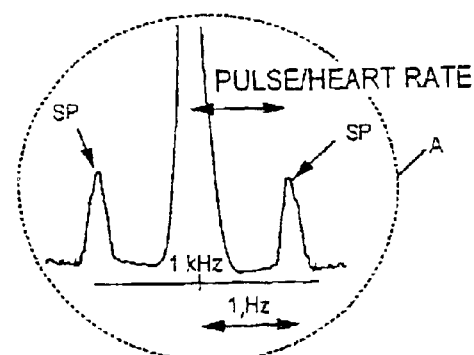
Figure 4A:
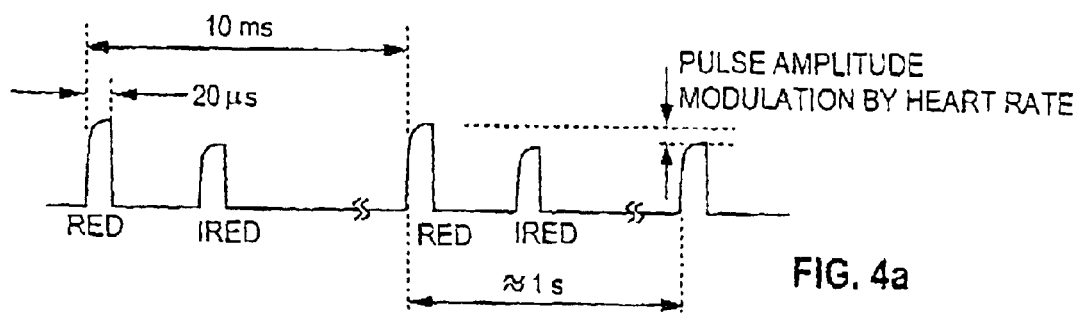
FIG. 4a illustrates the timing sequence of the detector signal when a low duty cycle pulse sequence is used.
Figure 4B:
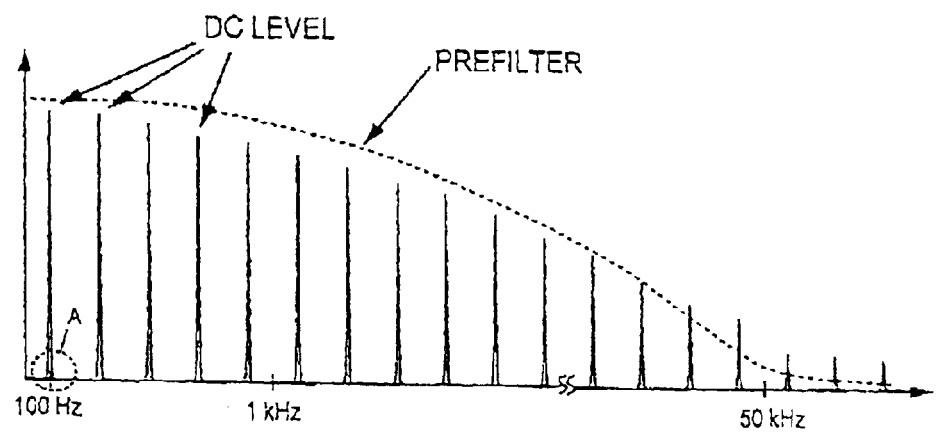
FIGS. 4b and 4c illustrate the frequency spectrum of a detector signal according to FIG. 4a, and FIG. 4d illustrates the spectrum of the baseband signal obtained from the signal of FIG. 4b after demodulation.
Figure 4C:
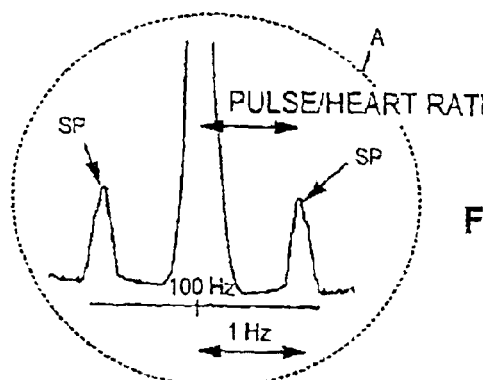

It is assumed here that (1) in the high duty cycle mode the pulse width equals 200 $\mu$s and the pulse repetition rate $f_r$ is equal to 1 kHz, i.e. the time period between two consecutive pulses is 1 ms, and (2) in the power saving mode the pulse width is equal to 20 $\mu$s and the pulse repetition rate $f_r$ equals 100 Hz. FIGS. 3a and 4a show the timing sequences of the detector signal in the respective modes, whereas FIGS. 3b and 4b illustrate the frequency spectrum of the detector signal in the respective modes. FIGS. 3a and 4a also show the amplitude modulation appearing in the pulse train at the heart rate of the patient. FIGS. 3c and 4c show in more detail the part of the spectrum denoted by circles A in FIGS. 3b and 4b, respectively.

As can be seen from FIGS. 3b, 3c, 4b, and 4c, the spectrum comprises a main peak at the pulse repetition frequency and harmonic peaks at the odd harmonic frequencies of the repetition rate. Side peaks SP caused by the above-mentioned amplitude modulation appear around the main and harmonic peaks. The frequency deviation between a side peak and the associated main or harmonic peak corresponds to the heart rate, which is in this context assumed to be 1 Hz.

Figure 3D:
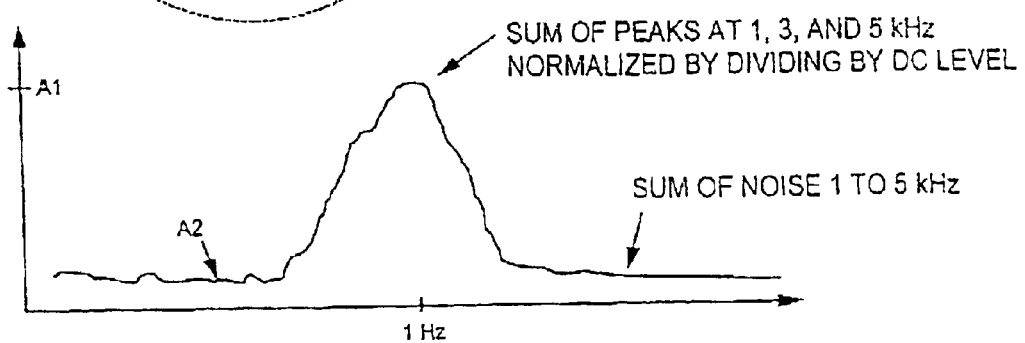
Figure 4D:
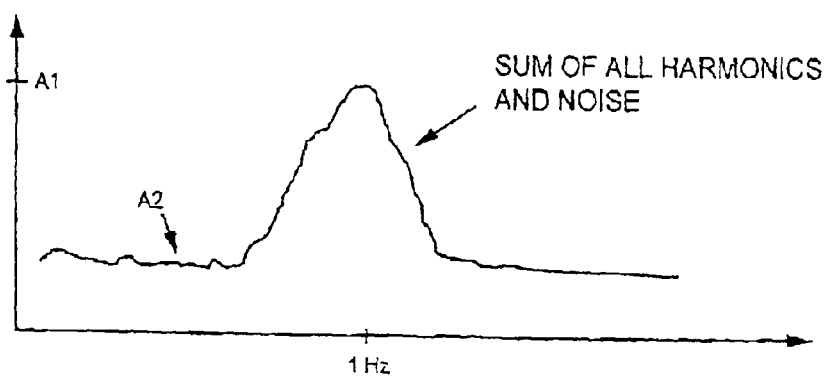

FIGS. 3d and 4d illustrate the frequency spectrum of the baseband signal in the above-mentioned two modes, i.e. the frequency spectrum of the signal after synchronous detection. The aliased peaks contribute to the amplitude A1 of the signal at the heart rate, whereas the surrounding noise level A2 is determined by the noise aliased on the whole band (FIG. 3d). The amplitude of the baseband signal (A1) indicates the perfusion level of the patient, but the quantity to be controlled is the baseband signal-to-noise ratio, which is directly dependent on the signal amplitude, i.e. on the perfusion level.

As to the power saving mode of FIG. 4a to 4d, narrowing the pulses and lowering their repetition rate has two consequences: the narrow pulses require the preamplifier to have a wide bandwidth, and the harmonic content of the detector signal is high (cf. FIG. 4b). When demodulating the narrow pulses, all harmonic components of the sampler are folded into the baseband. Therefore the noise level (A2) on the baseband (FIG. 4d) is higher than in the high duty cycle (FIG. 3d). In a sense the pulse harmonics belong to the "payload signal", since they contribute to the amplitude A1 of the signal at the heart rate, whereas the noise coming from the detector, the preamplifier, or other sources do not.

The dashed lines in FIGS. 3b and 4b illustrate the passband of the low-pass filter 13b contained in the amplifier stage, the passband being controlled by the control unit 18 in the above-described manner in association with the control of the pulse width. The actual width of the passband depends on many factors. However, the passband width is always kept at a value which allows the reception of a sufficient amount of pulse energy. As can be seen in FIG. 3c and 4c, the wider the pulses are the steeper the decline in harmonic amplitude.

It was assumed above that the pulse oximeter is a conventional pulse oximeter based on synchronous detection in the sampling units. However, the power control scheme of the invention can also be used with other types of pulse oximeters, for example, in a known oximeter based on fast A/D conversion.

Although the invention was described above with reference to the examples shown in the appended drawings, it is obvious that the invention is not limited to these, but may be modified by those skilled in the art without departing from the scope and spirit of the invention. For example, the pulse oximeter can be provided with more than two wavelengths and with auxiliary means for eliminating external interference, such as motion artifact. The number of distinct power levels depends on the implementation and can vary to a great extent. For example, the number of possible pulse width values depends on the resolution of the pulse width modulator used. Furthermore, the method can also be used in devices other than pulse oximeters, devices measuring other substances in a similar manner, i.e. non-invasively by radiating the patient. An example of such measurement is non-invasive optical monitoring of glucose or bilirubin, or simply an optical pulse rate monitor.

What is claimed is:

1. A method for controlling optical power in a monitoring device intended for determining the amount of at least one light absorbing substance in a subject, the monitoring device comprising emitters for emitting radiation at a minimum of two wavelengths driving means for activating said emitters, and a detector for receiving said radiation at said wavelengths and for producing an electrical signal in response to the radiation, the method comprising the steps of supplying driving pulses from said driving means to the emitters, the pulses having predetermined characteristics determining the optical power of the device, demodulating the electrical signal originating from said detector whereby a baseband signal is obtained;

transforming the baseband signal into a frequency spectrum to identify an amplitude and a noise level of the baseband signal, whereby a signal-to-noise ratio of the amplitude to the noise for the baseband signal is obtained;

monitoring the signal-to-noise ratio of the baseband signal, and controlling the duty cycle of the driving pulses in dependence on the monitored signal-to-noise ratio.

2. A method according to claim 1, wherein said controlling step includes controlling the duty cycle of the driving pulses so that the signal to noise ratio is maintained within the confines of a predetermined range for the signal-to-noise ratio.

3. A method according to claim 2, wherein said controlling step further includes comparing the monitored signal-to-noise ratio to said predetermined range, said predetermined range being defined by a predetermined lower threshold and a predetermined higher threshold.

4. A method according to claim 3, further including the step of connecting the electrical signal originating from said detector through a preamplifier and a low-pass-filter prior to said demodulating step.

5. A method according to claim 4, wherein said controlling step includes performing at least one operation in response to said signal-to-noise ratio reaching said lower threshold, the said at least one operation being selected from a group of operations including (1) the increase of the width of said pulses and (2) the increase of pulse repetition rate, and decreasing the bandwidth of said low-pass filter when the width of said pulses is increased.

6. A method according to claim 5, wherein the controlling step further includes the step of increasing the amplitude of said driving pulses.

7. A method according to claim 4, wherein said controlling step includes selecting at least one operation in response to said signal-to-noise ratio reaching said higher threshold, the said at least one operation being selected from a group of operations including (1) the decrease of the width of said pulses and (2) the decrease of pulse repetition rate, and increasing the bandwidth of said low-pass filter when the width of said pulses is decreased.

8. A method according to claim 7, wherein the controlling step further includes the step of decreasing the amplitude of said driving pulses.

9. A method according to claim 1, wherein said demodulating step includes sampling of the electrical signal by a synchronous detector, taking one sample per each pulse of the electrical signal.

10. A method according to claim 1, wherein the amount of at least one light absorbing substance is determined in the blood of a subject.

11. A method according to claim 1, wherein the monitoring device is a pulse oximeter.

12. An apparatus for non-invasively determining the amount of at least one light absorbing substance in a subject, the apparatus comprising emitters for emitting radiation at a minimum of two different wavelengths, driving means for activating said emitters, adapted to supply driving pulses to the emitters, the pulses having predetermined characteristics determining current optical power of the device, a detector for receiving said radiation at said wavelengths and producing an electrical signal in response to the radiation, a demodulator unit for demodulating the electrical signal originating from the detector, whereby a baseband signal is obtained from the demodulator unit, monitoring means for:
    transfoming the baseband signal into a frequency spectrum;
    generating a signal-to-noise ratio of the transformed baseband signal; and
    monitoring the signal-to-noise ratio of the baseband signal, and
power control means, responsive to the monitoring means, for controlling the duty cycle of the driving pulses.

13. An apparatus according to claim 12, wherein the power control means are adapted to control the duty cycle so that the signal-to-noise ratio is maintained within a predetermined range between a first threshold and a second threshold.

14. An apparatus according to claim 13, further comprising a low-pass filter for filtering said electrical signal prior to said demodulating, the control means comprising at least one set of first and second means, wherein the first means are adapted to change the width of said pulses and of the passband of the low-pass filter, and the second means are adapted to increase pulse repetition rate.

15. An apparatus according to claim 14, wherein the control means further comprise means for changing the amplitude of said pulses.

16. An apparatus according to claim 13, wherein said apparatus is a pulse oximeter.

17. A method for controlling optical power in a monitoring device intended for determining the amount of at least one light absorbing substance in a subject, the monitoring device comprising
    emitters for emitting radiation at a minimum of two wavelengths,
    driving means for activating said emitters, and
    a detector for receiving said radiation at said wavelengths and for producing an electrical signal in response to the radiation,
    the method comprising the steps of
    supplying driving pulses from said driving means to the emitters, the pulses having predetermined characteristics determining the optical power of the device,
    demodulating the electrical signal originating from said detector to generate demodulated signals for said wavelengths;
    obtaining a DC signal component for at least one of said demodulated signals;
    monitoring a signal-to-noise ratio of the DC signal component, and
    controlling the duty cycle of the driving pulses in dependence on the monitored signal-to-noise ratio of the DC signal component.

18. A method according to claim 17, wherein said controlling step includes controlling the duty cycle of the driving pulses so that the signal to noise ratio is maintained within the confines of a predetermined range for the signal-to-noise ratio.

19. A method according to claim 18, wherein said controlling step further includes comparing the monitored signal-to-noise ratio to said predetermined range, said predetermined range being defined by a predetermined lower threshold and a predetermined higher threshold.

20. A method according to claim 19, further including the step of connecting the electrical signal originating from said detector through a preamplifier and a low-pass-filter prior to said demodulating step.

21. A method according to claim 20, wherein said controlling step includes
    performing at least one operation in response to said signal-to-noise ratio reaching said lower threshold, the said at least one operation being selected from a group of operations including (1) the increase of the width of said pulses and (2) the increase of pulse repetition rate, and
    decreasing the bandwidth of said low-pass filter when the width of said pulses is increased.

22. A method according to claim 21, wherein the controlling step further includes the step of increasing the amplitude of said driving pulses.

23. A method according to claim 20, wherein said controlling step includes
    selecting at least one operation in response to said signal-to-noise ratio reaching said higher threshold, the said at least one operation being selected from a group of operations including (1) the decrease of the width of said pulses and (2) the decrease of pulse repetition rate, and
    increasing the bandwidth of said low-pass filter when the width of said pulses is decreased.

24. A method according to claim 23, wherein the controlling step further includes the step of decreasing the amplitude of said driving pulses.

25. A method according to claim 17, wherein said demodulating step includes sampling of the electrical signal by a synchronous detector, taking one sample per each pulse of the electrical signal.

26. A method according to claim 17, wherein the amount of at least one light absorbing substance is determined in the blood of a subject.

27. A method according to claim 17, wherein the monitoring device is a pulse oximeter.

28. An apparatus for non-invasively determining the amount of at least one light absorbing substance in a subject, the apparatus comprising
    emitters for emitting radiation at a minimum of two different wavelengths,
    driving means for activating said emitters, adapted to supply driving pulses to the emitters, the pulses having predetermined characteristics determining current optical power of the device,
    a detector for receiving said radiation at said wavelengths and producing an electrical signal in response to the radiation,
    a demodulator unit for demodulating the electrical signal originating from the detector to generate demodulated signals for said wavelengths, whereby a DC signal component of at least one of said demodulated signals is obtained from the demodulator unit,
    monitoring means for monitoring a signal-to-noise ratio of the DC signal component, and
    power control means, responsive to the monitoring means, for controlling the duty cycle of the driving pulses.

29. An apparatus according to claim 28, wherein the power control means are adapted to control the duty cycle so that the signal-to-noise ratio is maintained within a predetermined range between a first threshold and a second threshold.

30. An apparatus according to claim 29, further comprising a low-pass filter for filtering said electrical signal prior to said demodulating, the control means comprising at least one set of first and second means, wherein the first means are adapted to change the width of said pulses and of the passband of the low-pass filter, and the second means are adapted to increase pulse repetition rate.

31. An apparatus according to claim 30, wherein the control means further comprise means for changing the amplitude of said pulses.

32. An apparatus according to claim 29, wherein said apparatus is a pulse oximeter.

* * * * *

UNITED STATES PATENT AND TRADEMARK OFFICE
CERTIFICATE OF CORRECTION

PATENT NO. : 6,912,413 B2
DATED : June 28, 2005
INVENTOR(S) : Rantala et al.

It is certified that error appears in the above-identified patent and that said Letters Patent is hereby corrected as shown below:

Column 2,
Line 1, delete "carboxyhemogiobin" and insert therefor -- carboxyhemoglobin --.

Column 9,
Line 2, delete "transfoming", and insert therefor -- transforming --.

Signed and Sealed this

Sixteenth Day of August, 2005

JON W. DUDAS
*Director of the United States Patent and Trademark Office*